(12) United States Patent
Chen et al.

(10) Patent No.: US 11,583,363 B2
(45) Date of Patent: Feb. 21, 2023

(54) HOLDING MECHANISM FOR SURGICAL INSTRUMENTS AND HOLDING MODULE THEREOF

(71) Applicant: METAL INDUSTRIES RESEARCH & DEVELOPMENT CENTRE, Kaohsiung (TW)

(72) Inventors: Ming-Hui Chen, Kaohsiung (TW); Kai-Szu Lo, Tainan (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 281 days.

(21) Appl. No.: 17/029,167

(22) Filed: Sep. 23, 2020

(65) Prior Publication Data

US 2022/0087775 A1 Mar. 24, 2022

(51) Int. Cl.
| | |
|---|---|
| *A61B 90/50* | (2016.01) |
| *B25J 9/10* | (2006.01) |
| *A61B 90/00* | (2016.01) |
| *A61B 90/10* | (2016.01) |

(52) U.S. Cl.
CPC .............. *A61B 90/50* (2016.02); *A61B 90/03* (2016.02); *A61B 90/10* (2016.02); *B25J 9/1035* (2013.01)

(58) Field of Classification Search
CPC ......... A61B 90/50; A61B 90/03; A61B 90/10; A61B 90/11; A61B 34/37; A61B 34/30; A61B 34/70; A61B 34/71; A61B 34/72; A61B 34/77; A61B 2034/305; A61B 2034/732; A61B 2034/733; A61B 2034/306; A61B 2034/302; A61B 2034/303; A61B 2034/304; A61B 2017/00477; B25J 9/1035

See application file for complete search history.

(56) References Cited

U.S. PATENT DOCUMENTS

| | | | | |
|---|---|---|---|---|
| 6,246,200 | B1* | 6/2001 | Blumenkranz | A61B 34/70 318/568.25 |
| 6,821,243 | B2* | 11/2004 | Pagliuca | A61B 90/50 600/102 |
| 2007/0156122 | A1* | 7/2007 | Cooper | B25J 19/0016 606/1 |

FOREIGN PATENT DOCUMENTS

| | | |
|---|---|---|
| CN | 208404842 U | 1/2019 |
| CN | 211213489 U | 8/2020 |
| CN | 211213489 U * | 8/2020 |

OTHER PUBLICATIONS

Taiwanese Office Action dated Oct. 30, 2020 for Taiwanese Patent Application No. 109129014, 5 pages.

* cited by examiner

*Primary Examiner* — Shaun L David
*Assistant Examiner* — Rachael L Geiger
(74) *Attorney, Agent, or Firm* — Demian K. Jackson; Jackson IPG PLLC (57) ABSTRACT

A mechanism for holding surgical instruments includes a carrier mounted on a machine tool and multiple holding modules mounted on the carrier. At least one of the holding modules is selected to be used during surgical operation. A swing element of the selected holding module enables a guidance sleeve to be swung to allow a guidance hole on the guidance sleeve to face toward a surgical operation region. The guidance sleeve is provided to hold one surgical instrument for surgical operation.

12 Claims, 6 Drawing Sheets

HOLDING MECHANISM FOR SURGICAL INSTRUMENTS AND HOLDING MODULE THEREOF

FIELD OF THE INVENTION

This invention generally relates to a holding mechanism, and more particularly to a holding mechanism for surgical instruments.

BACKGROUND OF THE INVENTION

Surgical accuracy and success rate are increased with medical advances, particularly improvement of surgical instruments. Some of surgical instruments, e.g. bone anchor, anchor clamp, soft tissue probe, spinal stabilizer and bone screw instrumentation for minimally invasive spinal surgery, need to be held by surgeon using a sleeve.

Conventionally, at least one surgical instrument has to be inserted into a guiding hole of the sleeve and held by the sleeve during surgical operation. However, multiple sleeves having different sizes of guiding holes may be required for replacement and assembly of different surgical instruments having different outer diameters, or more than one sleeves having the same size of guiding holes are required for surgical instruments with the same outer diameter. In practice, replacement of sleeves is annoying and time wasted during surgical procedures, furthermore, it may cause operation disorder with increased risk.

SUMMARY

The object of the present invention is to disclose a holding mechanism that includes a carrier and multiple holding modules mounted on the carrier. The carrier is mounted on a machine tool and at least one of the holding modules is selected to be used. In the selected holding module, a swing element is used to move a guidance sleeve to be positioned in a first position or a second position so as to allow a guidance hole on the guidance sleeve to face or not face toward a surgical operation region. A surgical instrument is able to be inserted into the guidance hole facing toward the surgical operation region and be held by the guidance sleeve for surgical operation. While sleeve replacement is required, another holding module mounted on the carrier is selected to hold another surgical instrument by using its guidance sleeve.

One aspect of the present invention provides a holding mechanism for surgical instruments. The holding mechanism includes a carrier mounted on a machine tool and multiple holding modules mounted on the carrier. At least one of the holding modules is selected to be used during surgical operation, and each of them includes a base, a swing element and a guidance sleeve. The base is mounted on the carrier, the swing element is pivotally mounted on the base and pivotally movable relative to the base, the guidance sleeve is connected to the swing element so as to be moved together with the swing element and be positioned in a first position or a second position. The guidance sleeve is used to hold a surgical instrument, and a guidance hole on the guidance sleeve faces toward a surgical operation region when the guidance sleeve is positioned in the second position.

Another aspect of the present invention provides a holding module of a holding mechanism for surgical instruments. The holding module includes a base, a swing element and a guidance sleeve. The swing element is pivotally mounted on the base and pivotally movable relative to the base. The guidance sleeve having a guidance hole is connected to the swing element and used to be moved together with the swing element to be positioned in a first position or a second position.

During surgical operation, at least one of the holding modules mounted on the carrier is selected to be used. The guidance sleeve of the selected holding module is swung by the swing element to allow the guidance hole of the guidance sleeve to face toward the surgical operation region such that the surgical instrument is able to be inserted through the guidance hole to be held. When another surgical instrument is required to be used, another holding module is selected and its guidance sleeve is moved to hold the required surgical instrument. The present invention can solve the problem of sleeve replacement.

DETAILED DESCRIPTION OF THE INVENTION

Figure 1:
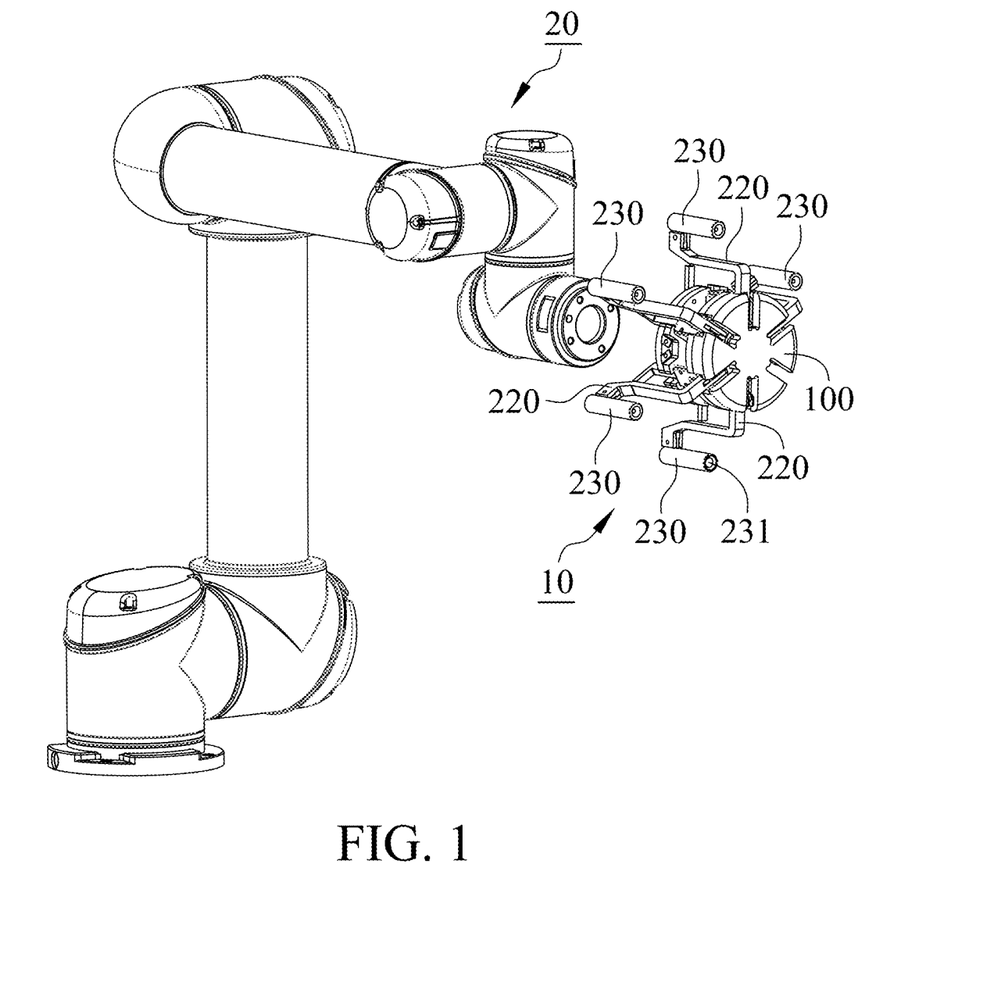
FIG. 1 is a perspective assembly diagram illustrating a holding mechanism mounted on a machine tool in accordance with one embodiment of the present invention.

With reference to FIG. 1, a holding mechanism 10 for surgical instruments is provided to be mounted on a machine tool 20 that is, but not limited to, a steering machine, like robotic arm.

Figure 2:
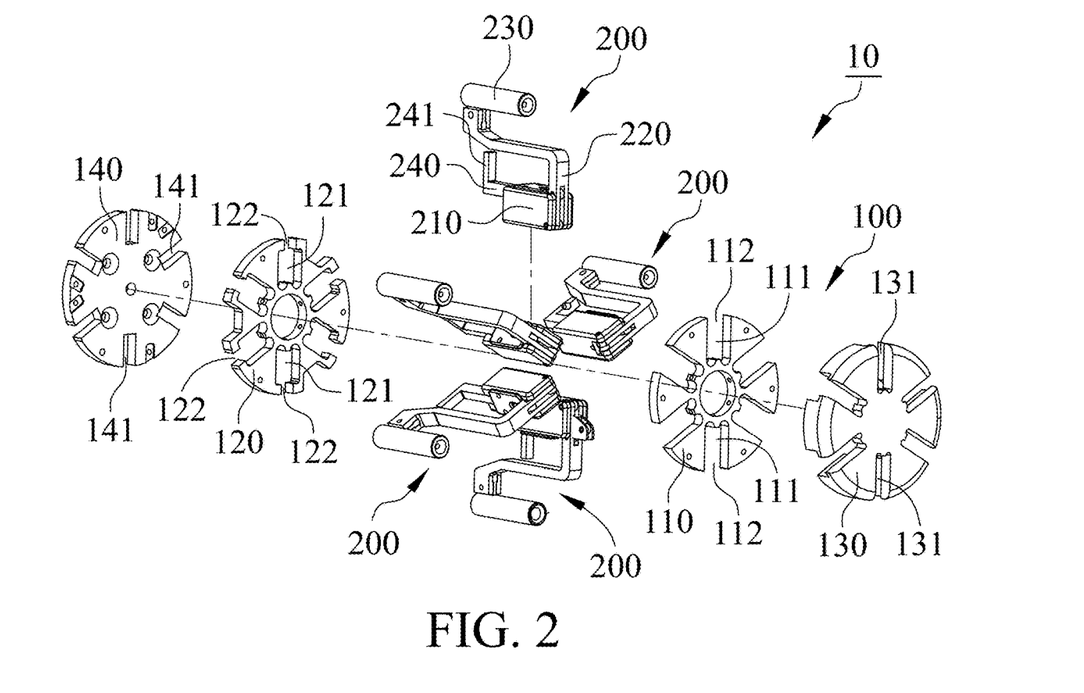
FIG. 2 is a perspective explored diagram illustrating a holding mechanism in accordance with one embodiment of the present invention.
Figure 3:
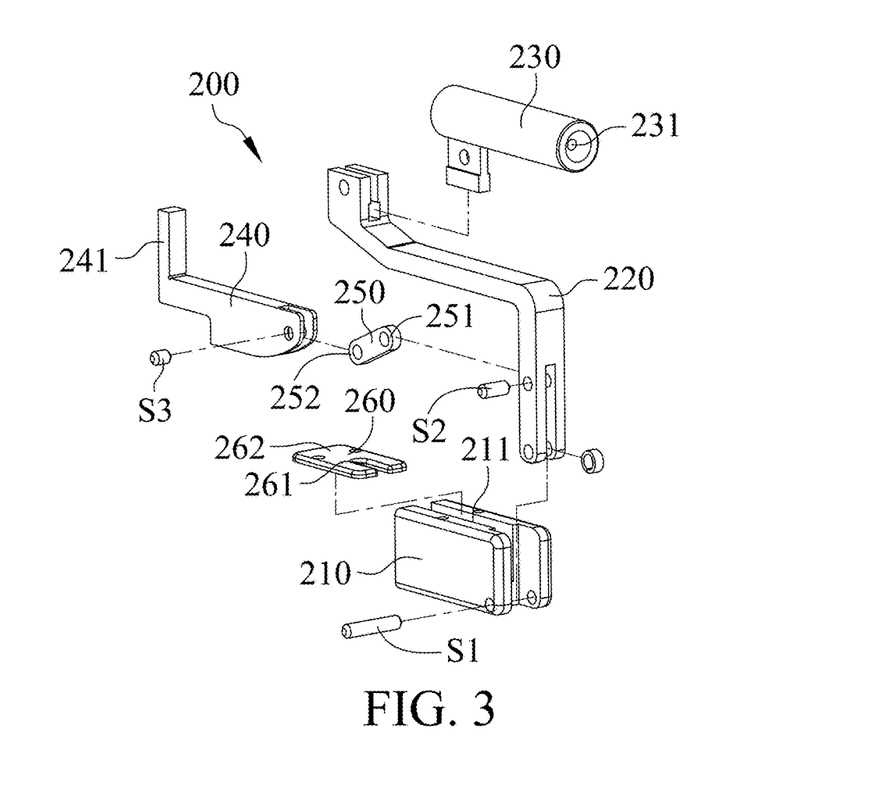
FIG. 3 is a perspective explored diagram illustrating a holding module in accordance with a first embodiment of the present invention.

With reference to FIGS. 1 and 2, the holding mechanism 10 includes a carrier 100 and multiple holding modules 200 that are mounted on the carrier 100. The carrier 100 is provided to be mounted on the machine tool 20 that is, but not limited to, a robotic arm able to move or rotate the holding mechanism 10.

With reference to FIGS. 1 and 2, bases 210 of the holding modules 200 are mounted on the carrier 100. In this embodiment, the carrier 100 includes a first carrier piece 110 where there are multiple first accommodation grooves 111 with radial arrangement, and the bases 210 of the holding modules 200 are placed in the first accommodation grooves 111, respectively. Each of the first accommodation grooves 111 includes a first yielding notch 112.

With reference to FIGS. 1 and 2, the carrier 100 further includes a second carrier piece 120 that is provided with multiple second accommodation grooves 121 having a radial arrangement. The bases 210 of the holding modules 200 are also placed in the second accommodation grooves 121, respectively. In this embodiment, the bases 210 of the holding modules 200 are clamped between the first carrier piece 110 and the second carrier piece 120. Preferably, the carrier 100 further includes a first cover 130 attached to the first carrier piece 110 and a second cover 140 attached to the second carrier piece 120.

As shown in FIGS. 3 to 7, each of the holding modules 200 of a first embodiment of the present invention includes a base 210, a swing element 220 and a guidance sleeve 230 having a guidance hole 231. In each of the holding modules 200, the base 210 is mounted on the carrier 100, and the swing element 220 is pivotally mounted on the base 210 such that it is pivotally movable relative to the base 210. The swing element 220 of the first embodiment is pivotally mounted on the base 210 via a first pivot rod S1.

Figure 4:
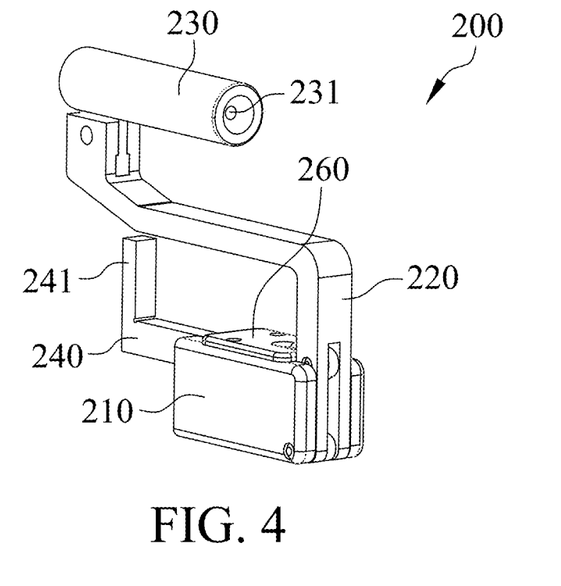
FIG. 4 is a perspective assembly diagram illustrating the holding module at a first position in accordance with the first embodiment of the present invention.
Figure 5:
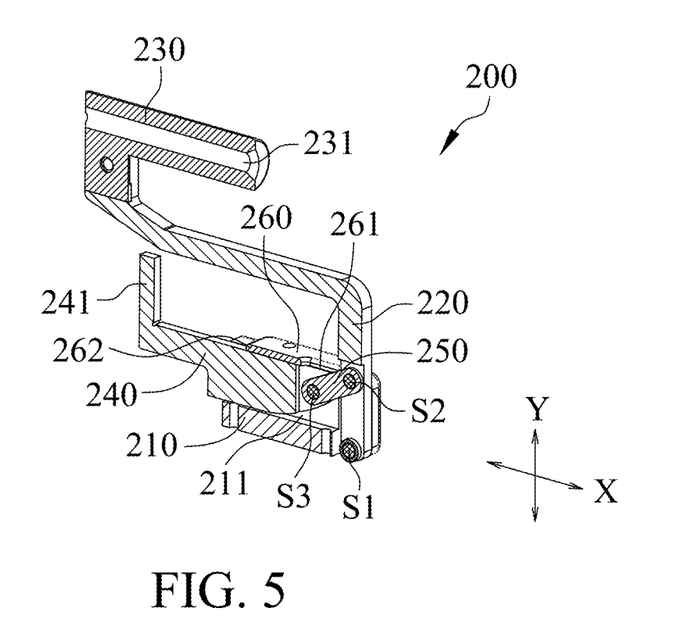
FIG. 5 is a perspective cross-section view of FIG. 4.
Figure 6:
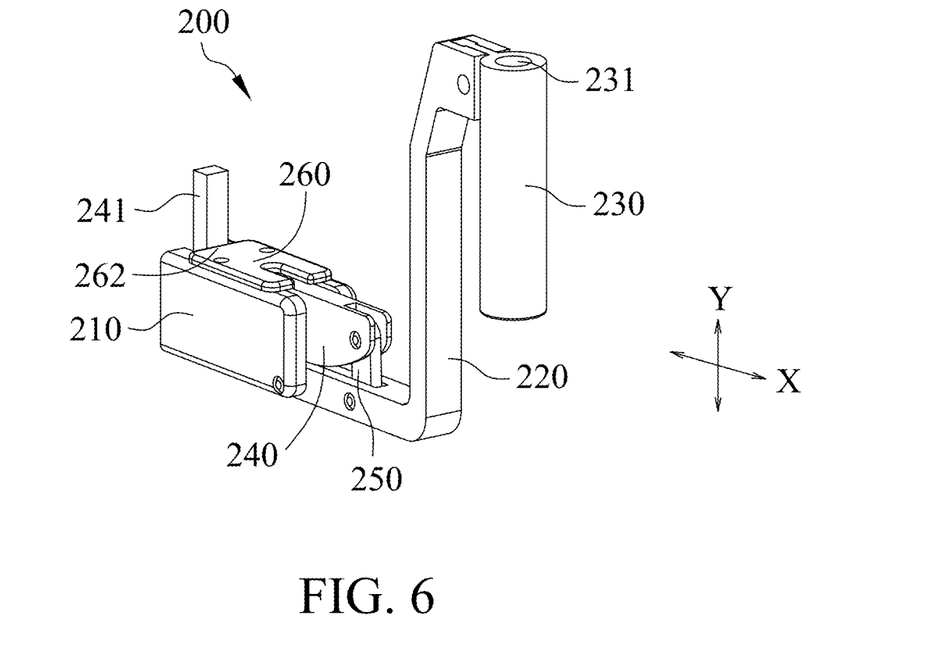
FIG. 6 is a perspective assembly diagram illustrating the holding module at a second position in accordance with the first embodiment of the present invention.
Figure 7:
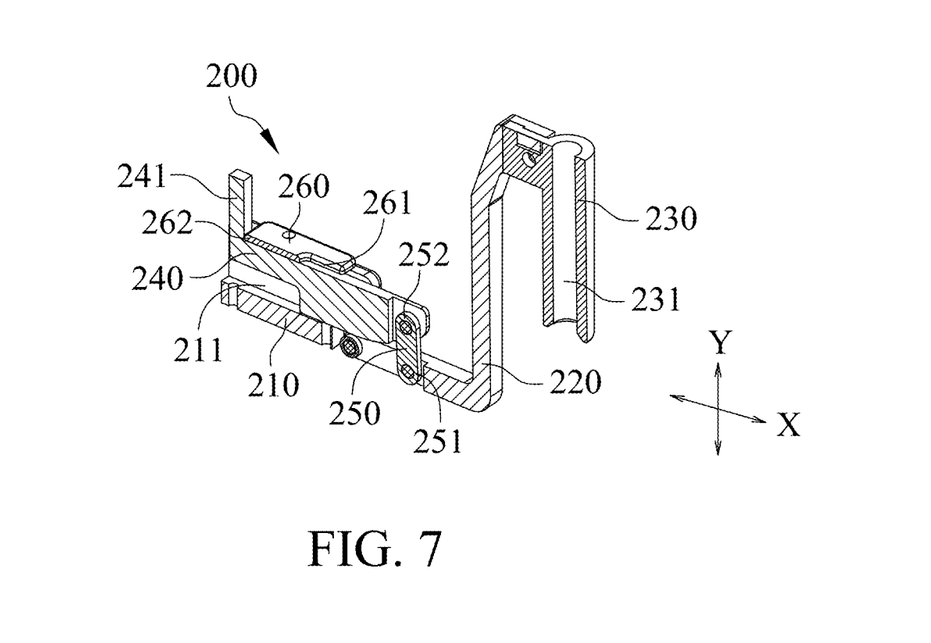
FIG. 7 is a perspective cross-section view of FIG. 6.

With reference to FIGS. 3 to 7, the guidance sleeve 230 is connected and moved together with the swing element 220 so as to be able to be positioned in a first position or a second position. In the first embodiment as shown in FIGS. 1 and 4, the guidance sleeve 230 is defined as located in the first position when its guidance hole 231 does not face toward a surgical operation region (not shown). In contrast, as shown in FIGS. 6 and 8, the guidance sleeve 230 is defined as located in the second position when the guidance hole 231 faces toward a surgical operation region (not shown).

With reference to FIGS. 3 to 7, each of the holding modules 200 of the first embodiment further includes a drive element 240 and a transmission element 250. The drive element 240 is mounted on the base 210 and movable along a first axis X, and a first end 251 and a second end 252 of the transmission element 250 are pivotally mounted on the swing element 220 and the drive element 240, respectively. In the first embodiment, the first end 251 of the transmission element 250 is pivotally mounted on the swing element 220 by a second pivot rod S2, and the second end 252 of the transmission element 250 is pivotally mounted on the drive element 240 by a third pivot rod S3.

Figure 8:
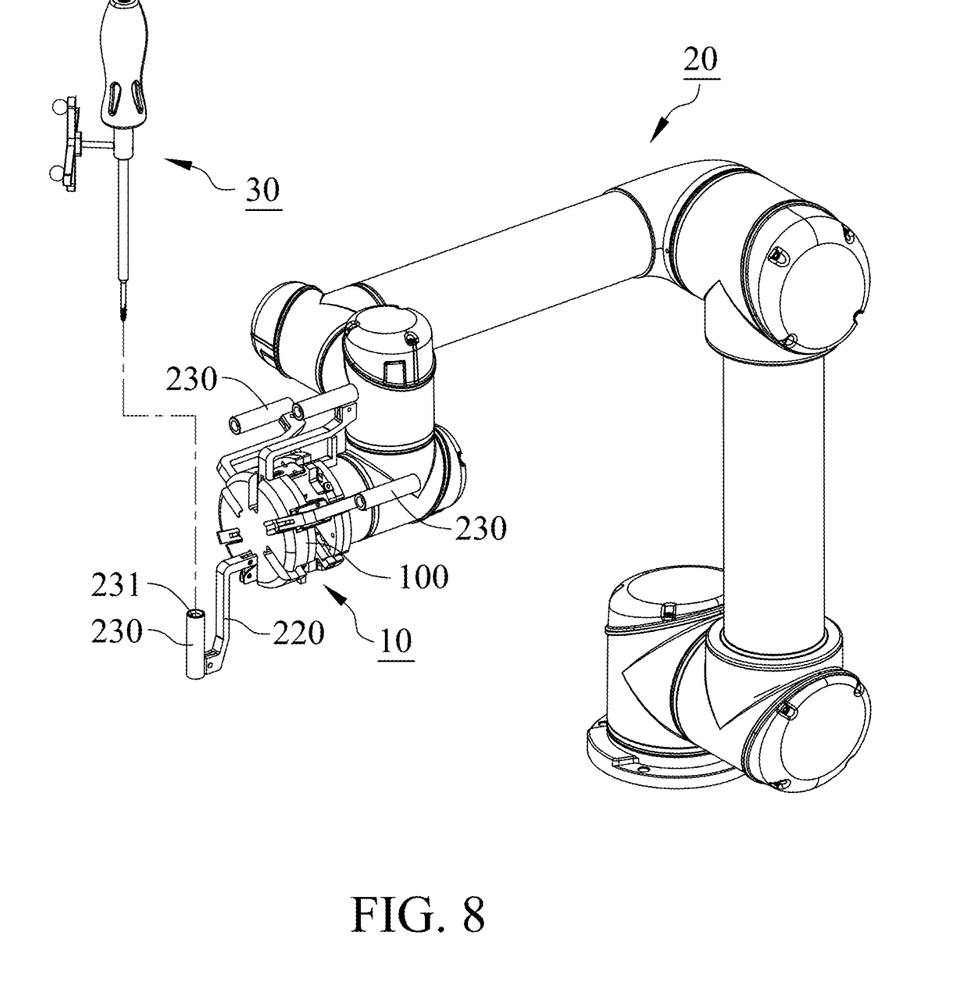
FIG. 8 is a perspective assembly diagram illustrating a surgical instrument mounted on a holding mechanism in accordance with the first embodiment of the present invention.

With reference to FIGS. 4 to 7, the drive element 240 is able to move the transmission element 250 along the first axis X to allow the swing element 220 to swing and further allow the guidance sleeve 230 moved together with the swing element 220 to move from the first position (as shown in FIGS. 1 and 4) to the second position (as shown in FIGS. 6 and 8). In the first embodiment as shown in FIGS. 1 and 4, the guidance sleeve 230 in the first position is located at one side of the carrier 100. On the other hand, the guidance sleeve 230 in the second position is located at the other side of the carrier 100 as shown in FIGS. 6 and 8.

With reference to FIGS. 2, 6 and 8, there are multiple first yielding grooves 131 radially arranged on the first cover 130, and the first yielding notch 112 of each of the first accommodation grooves 111 of the first carrier piece 110 and each of the first yielding grooves 131 of the first cover 130 together provide a path for the swing element 220 to travel. Consequently, the swing element 220 is able to pass through the first yielding notch 112 and the first yielding groove 131 when it is moved by the transmission element 250.

With reference to FIGS. 3 to 7, the drive element 240 is movably disposed in an accommodation space 211 of the base 210, each of the holding modules 200 further includes a limitation cover 260 that is provided to cover the accommodation space 211 along a second axis Y intersecting the first axis X. Thus the drive element 240 is restricted to move along the first axis X and is unable to depart from the accommodation space 211. Preferably, a yielding groove 261 is formed on the limitation cover 260 and provides a path for the second end 252 of the transmission element 250 to travel. While the transmission element 250 is moved by the drive element 240, the second end 252 of the transmission element 250 can pass through the yielding groove 261 such that the transmission element 250 is protected from collision with the limitation cover 260.

With reference to FIGS. 3 to 7, a stop portion 262 of the limitation cover 260 is located in a movement path of a limitation portion 241 of the drive element 240 so that the limitation portion 241 is able to be blocked by the stop portion 262 to allow the guidance sleeve 230 to be positioned in the second position.

With reference to FIGS. 1, 2, 4 and 8, each of the second accommodation grooves 121 of the second carrier piece 120 includes a second yielding notch 122, and multiple second yielding grooves 141 are radially arranged on the second cover 140. The second yielding notch 122 and the second yielding groove 141 together provide a path for the limitation portion 241 of the drive element 240 to travel, as a result, the limitation portion 241 can pass through the second yielding notch 122 and the second yielding groove 141 when the transmission element 250 enables the swing element 220 to swing.

The holding modules 200 are mounted on the carrier 100 to construct the holding mechanism 10 as shown in FIG. 1 and then can be used during surgical operation. In the holding mechanism 10, the guidance holes 231 of the guidance sleeves 230 may have the same diameter, or at least one (one or more than one) of the guidance holes 231 has a diameter different than that of the others, or all of the guidance holes 231 have different diameters. Next, the holding mechanism 10 is mounted on the machine tool 20 and the guidance sleeves 230 of the holding modules 200 are placed in the first position. Preferably, the machine tool 20 is a multi-axis robotic arm used to move the holding mechanism 10 to the surgical operation region and rotate the holding mechanism 10 to allow one of the holding modules 200 to be put in place for surgical operation. The guidance holes 231 of the guidance sleeves 230 located in the first position do not face toward the surgical operation region so as to prevent the guidance sleeves 230 from hitting healthcare worker or other machine tools while the holding mechanism 10 is rotated. In this embodiment, with reference to FIG. 8, when one of the holding modules 200 is set to be in place, the drive element 240 of the selected holding module 200 moves the transmission element 250 to allow the swing element 220 to be swung, thus, the guidance sleeve 230 is moved together with the swing element 220 to the second position and the guidance hole 231 of the guidance sleeve 230 faces toward the surgical operation region. Finally, a surgical instrument 30 is inserted into the guidance hole 231 and held by the guidance sleeve 230 for surgical operation.

Before the selected holding module 200 is replaced with another holding module 200, the swing element 220 of the selected holding module 200 is moved by the drive element 240 and the transmission element 250 such that the guidance sleeve 230 moved together with the swing element 220 is moved back to the first position from the second position. Afterward the machine tool 20 rotates the holding mechanism 10 to set another holding module 200 in place for holding another surgical instrument 30 for surgical operation.

Figure 9:
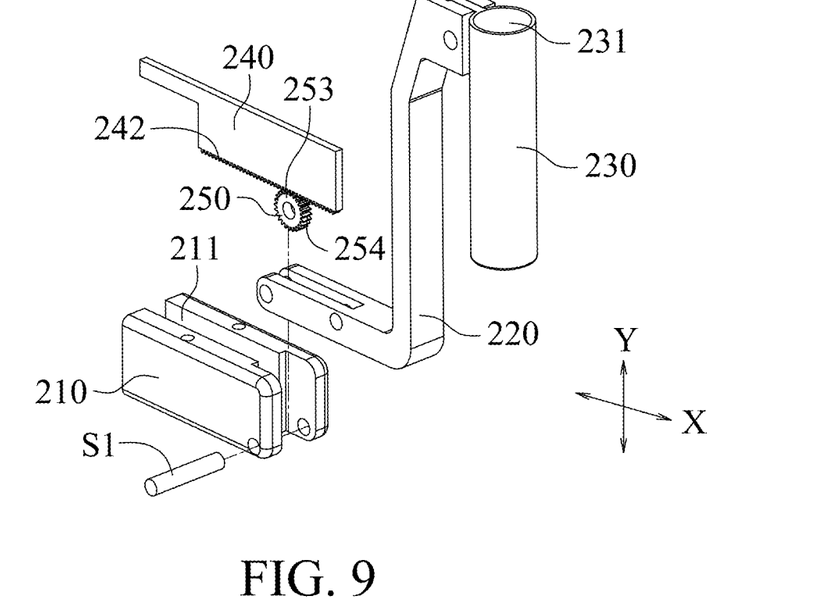
FIG. 9 is a perspective explored diagram illustrating a holding module in accordance with a second embodiment of the present invention.
Figure 10:
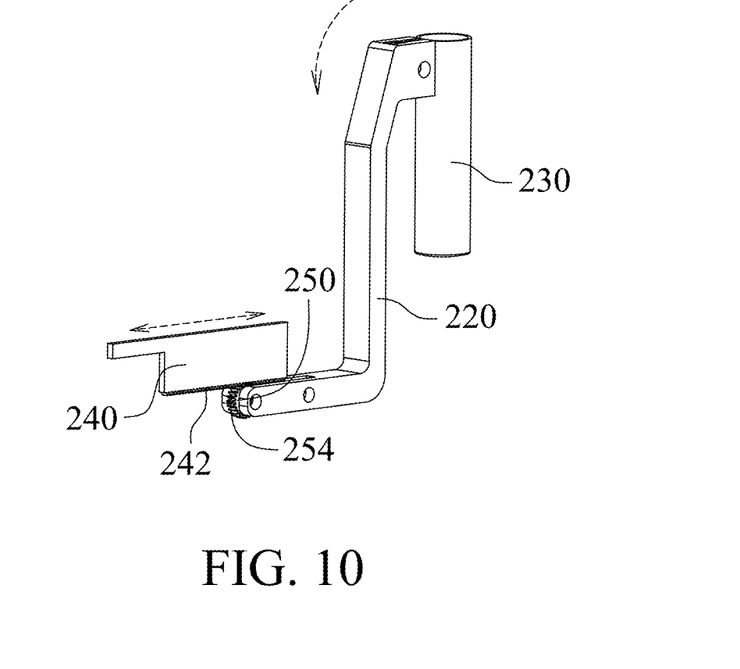
FIG. 10 is a partial perspective assembly diagram illustrating the holding module in accordance with the second embodiment of the present invention.

Holding modules 200 of a second embodiment of the present invention are represented in FIGS. 9 and 10. Different to the first embodiment, the transmission element 250 of the second embodiment is connected to the swing element 220, and the drive element 240 contacts a pushed portion 253 of the transmission element 250. In the second embodiment, the swing element 220 is also pivotally mounted on the base 210 by the first pivot rod S1 and the drive element 240 is also movably mounted on the base 210. However, the drive element 240 of the second embodiment is provided to push the pushed portion 253 of the transmission element 250 along the first axis X to swing the swing element 220.

With reference to FIGS. 9 and 10, preferably, there is a gear rack 242 on the drive element 240, the transmission element 250 is a gear having teeth 254 on the pushed portion 253, and the gear rack 242 and the teeth 254 are in mesh. Along the first axis X, the drive element 240 utilizes the gear rack 242 to move the transmission element 250 connected to the swing element 220, as a result, the guidance sleeve 230 is able to be moved to the first position or the second position together with the swing element 220.

With reference to FIG. 8, according to requirements of surgical operations, the holding modules 200 including the guidance sleeves 230 can be mounted on the carrier 100 in advance. Furthermore, one of the guidance sleeves 230 matching the outer diameter of a required surgical instrument is selected and moved by the swing element 220 so as to allow the guidance hole 231 of the selected guidance sleeve 230 to face toward surgical operation region for holding the required surgical instrument. The holding mechanism 10 of the present invention is a solution to solve a problem of sleeve replacement, and problems of operation disorder and time delay caused by mistake of sleeve replacement.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A holding mechanism for surgical instruments comprising:
    a carrier configured to be mounted on a machine tool; and
    a plurality of holding modules mounted on the carrier, at least one of the plurality of holding modules is selected to be used, each of the plurality of holding modules includes a base, a swing element and a guidance sleeve, the base is mounted on the carrier, the swing element is pivotally mounted on the base and pivotally movable relative to the base, the guidance sleeve is connected to the swing element so as to be moved together with the swing element and be positioned in a first position or a second position, the guidance sleeve is configured to hold a surgical instrument, wherein a guidance hole on the guidance sleeve faces toward a surgical operation region when the guidance sleeve is positioned in the second position, and wherein the carrier includes a first carrier piece, a plurality of first accommodation grooves are radially arranged on the first carrier piece, the base of each of the plurality of holding modules is located in each of the plurality of first accommodation grooves respectively, a first yielding notch of each of the plurality of first accommodation grooves is configured to provide a path for the swing element to pass.

2. The holding mechanism in accordance with claim 1, wherein the guidance hole of at least one of the plurality of holding modules has a diameter different from that of the other holding modules.

3. The holding mechanism in accordance with claim 1, wherein each of the plurality of holding modules further includes a drive element and a transmission element, the drive element is mounted on the base and movable along a first axis, a first end of the transmission element is pivotally mounted on the swing element and a second end of the transmission element is pivotally mounted on the drive element, the drive element is configured to move the transmission element along the first axis for the swing element to be swung.

4. The holding mechanism in accordance with claim 3, wherein each of the plurality of holding modules further includes a limitation cover, the drive element is movably mounted in an accommodation space of the base, the limitation cover is configured to cover the accommodation space along a second axis intersecting the first axis, a yielding groove on the limitation cover is configured to provide a path for the second end of the transmission element to pass.

5. The holding mechanism in accordance with claim 3, wherein each of the plurality of holding modules further includes a limitation cover, the drive element is movably mounted in an accommodation space of the base, the limitation cover is configured to cover the accommodation space along a second axis intersecting the first axis, a stop portion of the limitation cover is located in a movement path of a limitation portion of the drive element and configured to block the limitation portion.

6. The holding mechanism in accordance with claim 3, wherein the carrier includes a second carrier piece, a plurality of second accommodation grooves are radially arranged on the second carrier piece, the base of each of the plurality of holding modules is located in each of the plurality of second accommodation grooves respectively, a second yielding notch of each of the plurality of second accommodation grooves is configured to provide a path for a limitation portion of the drive element to pass.

7. The holding mechanism in accordance with claim 1, wherein each of the plurality of holding modules further includes a drive element and a transmission element, the drive element is mounted on the base and movable along a first axis, the transmission element is connected to the swing element and includes a pushed portion, the drive element is configured to contact and push the pushed portion along the first axis for the swing element to be swung.

8. The holding mechanism in accordance with claim 7, wherein a gear rack on the drive element and a plurality of teeth on the pushed portion are in mesh.

9. The holding mechanism in accordance with claim 7, wherein each of the plurality of holding modules further includes a limitation cover, the drive element is movably mounted in an accommodation space of the base, the limitation cover is configured to cover the accommodation space along a second axis intersecting the first axis, a stop portion of the limitation cover is located in a movement path of a limitation portion of the drive element and configured to block the limitation portion.

10. The holding mechanism in accordance with claim 7, wherein the carrier includes a second carrier piece, a plurality of second accommodation grooves are radially arranged on the second carrier piece, the base of each of the plurality of holding modules is located in each of the plurality of second accommodation grooves respectively, a second yielding notch of each of the plurality of second accommodation grooves is configured to provide a path for a limitation portion of the drive element to pass.

11. A holding mechanism for surgical instruments comprising:
a carrier configured to be mounted on a machine tool; and
a plurality of holding modules mounted on the carrier, at least one of the plurality of holding modules is selected to be used, each of the plurality of holding modules includes a base, a swing element and a guidance sleeve, the base is mounted on the carrier, the swing element is pivotally mounted on the base and pivotally movable relative to the base, the guidance sleeve is connected to the swing element so as to be moved together with the swing element and be positioned in a first position or a second position, the guidance sleeve is configured to hold a surgical instrument, wherein a guidance hole on the guidance sleeve faces toward a surgical operation region when the guidance sleeve is positioned in the second position,
wherein each of the plurality of holding modules further includes a drive element and a transmission element, the drive element is mounted on the base and movable along a first axis, a first end of the transmission element is pivotally mounted on the swing element and a second end of the transmission element is pivotally mounted on the drive element, the drive element is configured to move the transmission element along the first axis for the swing element to be swung,
wherein the carrier includes a second carrier piece, a plurality of second accommodation grooves are radially arranged on the second carrier piece, the base of each of the plurality of holding modules is located in each of the plurality of second accommodation grooves respectively, a second yielding notch of each of the plurality of second accommodation grooves is configured to provide a path for a limitation portion of the drive element to pass.

12. A holding mechanism for surgical instruments comprising:
a carrier configured to be mounted on a machine tool; and
a plurality of holding modules mounted on the carrier, at least one of the plurality of holding modules is selected to be used, each of the plurality of holding modules includes a base, a swing element and a guidance sleeve, the base is mounted on the carrier, the swing element is pivotally mounted on the base and pivotally movable relative to the base, the guidance sleeve is connected to the swing element so as to be moved together with the swing element and be positioned in a first position or a second position, the guidance sleeve is configured to hold a surgical instrument, wherein a guidance hole on the guidance sleeve faces toward a surgical operation region when the guidance sleeve is positioned in the second position,
wherein each of the plurality of holding modules further includes a drive element and a transmission element, the drive element is mounted on the base and movable along a first axis, the transmission element is connected to the swing element and includes a pushed portion, the drive element is configured to contact and push the pushed portion along the first axis for the swing element to be swung,
wherein the carrier includes a second carrier piece, a plurality of second accommodation grooves are radially arranged on the second carrier piece, the base of each of the plurality of holding modules is located in each of the plurality of second accommodation grooves respectively, a second yielding notch of each of the plurality of second accommodation grooves is configured to provide a path for a limitation portion of the drive element to pass.

* * * * *